United States Patent
Sia et al.

(10) Patent No.: US 6,395,714 B1
(45) Date of Patent: May 28, 2002

(54) EXPRESSING GP140 FRAGMENT OF PRIMARY HIV-1 ISOLATE

(75) Inventors: Charles D. Y. Sia, Thornhill; Shi Xian Cao, Etobicoke; Roy Persson, North York; Benjamin Rovinski, Thornhill, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/256,194

(22) Filed: Feb. 24, 1999

(51) Int. Cl.[7] .................. A61K 48/00; C12N 15/63; C12N 15/11

(52) U.S. Cl. ............ 514/44; 435/320.1; 435/455; 536/23.1; 536/23.7; 536/23.72

(58) Field of Search ............... 514/44; 435/320.1, 435/455; 536/23.1, 23.7, 23.72

(56) References Cited

U.S. PATENT DOCUMENTS

| | | | |
|---|---|---|---|
| 5,075,109 A | 12/1991 | Tice et al. | 424/88 |
| 5,151,264 A | 9/1992 | Samain et al. | 424/1.1 |
| 5,639,854 A | 6/1997 | Sia et al. | 530/324 |
| 5,759,769 A | 6/1998 | Sia et al. | 435/5 |
| 5,795,955 A | 8/1998 | Sia et al. | 530/324 |

FOREIGN PATENT DOCUMENTS

| | | |
|---|---|---|
| EP | 470980 | 2/1994 |
| WO | WO91/06282 | 5/1991 |
| WO | WO94/27435 | 12/1991 |
| WO | WO93/18055 | 9/1993 |
| WO | WO 93/18055 | 9/1993 |
| WO | WO93/24640 | 12/1994 |
| WO | WO94/28929 | 12/1994 |
| WO | WO 94/28929 | 12/1994 |
| WO | WO 97/31115 | 8/1997 |
| WO | WO97/31115 | 8/1997 |

OTHER PUBLICATIONS

Wang et al. (1993) PNAS, vol. 90, 415–4160.*
Verrier et al. (1997) PNAS, vol. 94, 9326–9331.*
Mustafa et al. (1997) Virology, vol. 229, 269–278.*
Yasutomi et al. (1995) J. Virol., vol. 69 (4), 2279–2284.*
B.J. Spalding. Biotechnology, vol. 10, pp. 24–28, 1992.
H.L. Robinson and C.A.T. Torres. Seminars in Immunology, vol. 9, pp. 271–283, 1997.
Ian A. Wilson and Daved H. Fremont. Seminars in Immunology, vol. 5, pp. 75–80, 1993.
Kristen Falk and Olaf Rotzschke. Seminars in Immunology. vol. 5, pp. 81–94, 1993.
Furth et al, Analytical Biochemistry, 1992, 205:365–368.
R. Pat Bucy et al, AIDS 2001, 15 (suppl 2):S36–S42.
Lu S. et al: Immunogenicity of DNA vaccines expressing human immunodeficiency virus type 1 envelope glycoprotein with and without deletions in the V½and V3 regions: Aids Research and Human Retroviruses, Jan. 20, 1998, (14(2) p. 151–5.
Yahi, N. et al: "Structural Variability of Env and Gag Gene products from a highly cytopathic strain of HIV–1"; Archives of Virology 1992, vol. 125, No. 1–4, pp. 287–298.
Verrier, Florence C., et al: "Antibodies to several conformation–dependent epitopes of gp120/gp41 inhibit CCR–5–dependent cell–to–cell fusion mediated by the native envelope glycoprotein of a primary macrophage–tropic HIV–1 isolate." Proceedings of the National Academy of Sciences of the United States of America 1997, vol. 94, No. 17, pp. 9326–9331.
O'Brien, W.A. et al: "HIV–1 Tropism for Mononuclear Phagocytes Can be Determined by Regions of GP120 Outside the CD–4 Binding Domain" Nature(London) 1990, vol. 348, No. 6296, pp. 69–73.
Embl Database: Accession No. U63632, Aug. 30, 1996.
Victor H. Englefard. Current Opinion in Immunology, vol. 6, pp. 13–23, 1994.
Tang et al, Nature, 1992, 356:152–154.

* cited by examiner

*Primary Examiner*—Scott D. Priebe
*Assistant Examiner*—Anne Marie S. Beckerleg
(74) *Attorney, Agent, or Firm*—Sim & McBurney (57) ABSTRACT

A vector for eliciting an immune response to a host comprising a gene encoding the gp140 protein of the primary isolate of HIV-1, BX08, under the control of a promotor for expression of the protein in the host, specifically plasmid pCMV.gp140.BX08. Murine and human MHC class 1-restricted binding motifs contained in BX08 are identified.

7 Claims, 9 Drawing Sheets

```
+1    M   D   A   M   K   R   G   L   C   C   V   L   L   L   G
1    ATG GAT GCA ATG AAG AGA GGG CTC TGC TGT GTG CTG CTG CTG GGA
     TAC CTA CGT TAC TTC TCT CCC GAG ACG ACA CAC GAC GAC GAC CCT

+1    A   V   F   V   S   A   S   L   W   V   T   Y   Y   G   V
49   GCA GTC TTC GTT TCG GCT AGC TTG TGG GTC ACA TAT TAT GGG GTA
     CGT CAG AAG CAA AGC CGA TCG AAC CAG TGT ATA ATA CCC CAT

+1    P   V   W   K   E   A   Y   D   T   L   F   C   A   S   D   A
97   CCT GTG TGG AAA GAA GCA TAT GAT ACA CTA TTT TGT GCA TCA GAT GCT
     GGA CAC ACC TTT CTT CGT ATA CTA TGT GAT AAA ACA CGT AGT CTA CGA

+1    K   A   Y   D   T   E   V   H   N   V   W   A   T   H   A   C
145  AAA GCA TAT GAT ACA GAA GTA CAT AAT GTT TGG GCC ACA CAT GCC TGT
     TTT CGT ATA CTA TGT CTT CAT GTA TTA CAA ACC CGG TGT GTA CGG ACA

+1    V   P   T   D   P   N   P   Q   E   V   L   G   N   V   T
193  GTA CCC ACA GAC CCC AAC CCA CAA GAA GTA TTG GGA AAT GTG ACA
     CAT GGG TGT CTG GGG TTG GGT GTT CTT CAT AAC CCT TTA CAC TGT

+1    E   N   F   N   M   G   K   N   N   M   V   E   Q   M   H   E
241  GAA AAT TTT AAC ATG GGG AAA AAT AAC ATG GTA GAA CAG ATG CAT GAA
     CTT TTA AAA TTG TAC CCC TTT TTA TTG TAC CAT CTT GTC TAC GTA CTT

+1    D   I   S   L   W   D   Q   S   L   K   P   C   V   K   L
289  GAT ATA AGT TTA TGG GAT CAA AGC CTA AAG CCA TGT GTA AAA TTA
     CTA TAT TCA AAT ACC CTA GTT TCG GAT TTC GGT ACA CAT TTT AAT
```

FIG.2B

```
      T   P   L   C   V   T   L   N   C   T   K   L   K   N   S   T
 +1  ACC CCA CTC TGT GTT ACT TTA AAT TGC ACT AAG TTG AAG AAT AGT ACT
337  TGG GGT GAG ACA CAA TGA AAT TTA ACG TGA TTC AAC TTC TTA TCA TGA

D   T   N   N   T   R   W   G   T   Q   E   M   K   N   C   S
 +1  GAT ACC AAT AAT ACT AGA TGG GGA ACA CAA GAA ATG AAA AAC TGC TCT
385  CTA TGG TTA TTA TGA TCT ACC CCT GTT CTT TAC TTT TTG ACG AGA

F   N   I   S   T   S   V   R   N   K   M   K   R   E   Y   A
 +1  TTC AAC ATC AGC ACA AGT GTA AGA AAT AAG ATG AAG AGA GAA TAT GCA
433  AAG TTG TAG TCG TGT TCA CAT TCT TTA TTC TAC TTC TCT CTT ATA CGT

L   F   Y   S   L   D   I   V   P   I   D   N   D   N   T   S
 +1  CTT TTT TAT AGT CTT GAT ATA GTA CCA ATA GAT AAT GAT AAT ACT AGC
481  GAA AAA ATA TCA GAA CTA TAT CAT GGT TAT CTA TTA CTA TTA TGA TCG

Y   R   L   R   S   C   N   T   S   I   I   T   Q   A   C   P
 +1  TAT AGG TTA AGA AGT TGT AAT ACC TCA ATC ATT ACA CAG GCC TGT CCA
529  ATA TCC AAT TCT TCA ACA TTA TGG AGT TAG TAA TGT GTC CGG ACA GGT

K   V   S   F   E   P   I   P   I   H   F   C   A   P   A   G
 +1  AAG GTA TCC TTT GAG CCA ATT CCC ATA CAT TTT TGT GCC CCG GCT GGT
577  TTC CAT AGG AAA CTC GGT TAA GGG TAT GTA AAA ACA CGG GGC CGA CCA

F   A   I   L   K   C   N   N   K   T   F   N   G   T   G   P
 +1  TTT GCG ATT CTA AAG TGT AAT AAT AAA ACG TTC AAT GGA ACA GGA CCA
625  AAA CGC TAA GAT TTC ACA TTA TTA TTT TGC AAG TTA CCT TGT CCT GGT
```

FIG.2C

```
     C   T   N   V   S   T   V   Q   C   T   H   G   I   R   P   V
+1  TGT ACA AAT GTC AGC ACA GTA CAA TGT ACA CAT GGA ATT AGG CCA GTA
673 ACA TGT TTA CAG TCG TGT CAT GTT ACA TGT GTA CCT TAA TCC GGT CAT

V   S   T   Q   L   L   N   G   S   L   A   E   E   E   V
+1  GTA TCA ACT CAA CTG CTG TTA AAT GGC AGC CTA GCA GAA GAA GAG GTA
721 CAT AGT TGA GTT GAC GAC AAT TTA CCG TCG GAT CGT CTT CTT CTC CAT

V   I   R   S   E   N   F   T   N   N   A   K   T   I   I   V
769 GTA ATT AGA TCT GAA AAT TTC ACA AAC AAT GCT AAA ACC ATA ATA GTA
    CAT TAA TCT AGA CTT TTA AAG TGT TTG TTA CGA TTT TGG TAT TAT CAT

Q   L   N   E   S   V   E   I   N   C   T   R   P   N   N   N
817 CAG CTA AAT GAA TCT GTA GAA ATT AAT TGT ACA AGA CCC AAC AAC AAT
    GTC GAT TTA CTT AGA CAT CTT TAA TTA ACA TGT TCT GGG TTG TTG TTA

T   R   K   S   I   H   I   G   P   G   R   A   F   Y   T   T
865 ACA AGA AAA AGT ATA CAT ATA GGA CCA GGG AGA GCA TTT TAT ACA ACA
    TGT TCT TTT TCA TAT GTA TAT CCT GGT CCC TCT CGT AAA ATA TGT TGT

G   D   I   I   G   D   I   R   Q   A   H   C   N   I   S   R
913 GGA GAT ATA ATA GGA GAT ATA AGA CAA GCA CAT TGT AAC ATT AGT AGA
    CCT CTA TAT TAT CCT CTA TAT TCT GTT CGT GTA ACA TTG TAA TCA TCT

T   N   W   T   N   T   L   K   V   A   E   K   L   R   E
961 ACA AAC TGG ACT AAC ACT TTA AAA GTA GCT GAA AAA TTA AGA GAA
    TGT TTG ACC TGA TTG TGA AAT TTT CAT CGA CTT TTT AAT TCT CTT
```

FIG.2D

```
+1     K   F   N   N   T   I   V   F   N   Q   S   G   G   D
1009   AAA TTT AAT AAT ACA ATA GTC TTT AAT CAA TCC GGA GGG GAC
       TTT AAA TTA TTA TGT TAT CAG AAA TTA GTT AGG CCT CCC CTG

+1     P   E   I   V   M   H   S   F   N   C   G   E   F   Y
1057   CCA GAA ATT GTA ATG CAC AGT TTT AAT TGT GGA GGG GAA TTT TAC
       GGT CTT TAA CAT TAC GTG TCA AAA TTA ACA CCT CCC CTT AAA AAG ATG

+1     C   N   T   T   Q   L   F   N   S   T   W   N   E   T   N   S
1105   TGT AAT ACA ACA CAA CTG TTT AAT AGT ACT TGG AAT GAA ACT AAC AGT
       ACA TTA TGT TGT GTT GAC AAA TTA TCA TGA ACC TTA CTT TGA TTG TCA

+1     E   G   N   I   T   S   G   T   I   T   L   P   C   R   I   K
1153   GAA GGA AAT ATC ACC AGT GGA ACT ATA ACA CTC CCA TGC AGA ATA AAA
       CTT CCT TTA TAG TGG TCA CCT TGA TAT TGT GAG GGT ACG TCT TAT TTT

+1     Q   I   I   N   M   W   Q   E   V   G   K   A   M   Y   A   P
1201   CAA ATT ATA AAC ATG TGG CAG GAA GTA GGA AAA GCA ATG TAT GCC CCT
       GTT TAA TAT TTG TAC ACC GTC CTT CAT CCT TTT CGT TAC ATA CGG GGA

+1     P   I   G   G   Q   I   K   C   L   S   N   I   T   G   L   L
1249   CCC ATC GGA GGA CAA ATT AAA TGT TCA AAC ATC ACA GGG CTG TTA
       GGG TAG CCT CCT GTT TAA TTT ACA AGT TTG TAG TGT CCC GAC AAT

+1     L   T   R   D   G   G   S   D   N   S   S   G   K   E   I
1297   TTA ACA AGA GAT GGT GGT AGT GAT AAC AGT AGT GGG AAA GAG ATC
       AAT TGT TCT CTA CCA CCA TCA CTA TTG TCA TCA CCC TTT CTC TAG
```

FIG.2E

```
+1    F   R   P   G   G   D   M   R   D   N   W   R   S   E   L
1345  TTC AGA CCT GGA GGG GAT ATG AGG GAC AAT TGG AGA AGT GAA TTA
      AAG TCT GGA CCT CCC CTA TAC TCC CTG TTA ACC TCT TCA CTT AAT

+1    Y   K   Y   K   V   V   K   I   E   P   L   G   I   A   P   T
1393  TAT AAA TAT AAG GTA GTG AAA ATT GAA CCA TTA GGA ATA CCC ACC
      ATA TTT ATA TTC CAT CAC TTT TAA CTT GGT AAT CCT TAT GGG TGG

+1    K   A   K   R   R   V   Q   R   E   K   R   A   V   G   I
1441  AAG GCA AAG AGA AGA GTG CAG AGA GAA AAA AGA GCA GTG GGA ATA
      TTC CGT TTC TCT TCT CAC GTC TCT CTT TTT TCT CGT CAC CCT TAT

+1    G   A   M   F   L   G   F   L   T   V   Q   A   R   T   M   G
1489  GGA GCC ATG TTC CTT GGG TTC CTG ACG GTA CAG GCA GGA ACT ATG GGC
      CCT CGG TAC AAG GAA CCC AAG GAC TGC CAT GTC CGT CCT TGA TAC CCG

+1    A   A   S   L   T   L   T   V   Q   A   R   Q   L   L   S   G
1537  GCA GCG TCA CTA ACG CTG ACG GTA CAG GCA AGA CAA TTA TTG TCT GGT
      CGT CGC AGT GAT TGC GAC TGC CAT GTC CGT TCT GTT AAT AAC AGA CCA

+1    I   V   Q   Q   Q   N   N   L   L   R   A   I   E   A   Q   Q
1585  ATA GTG CAG CAG CAG AAC AAT TTG CTG AGG GCT ATT GAG GCG CAA CAG
      TAT CAC GTC GTC GTC TTG TTA AAC GAC TCC CGA TAA CTC CGC GTT GTC

+1    H   L   L   Q   L   T   V   W   G   I   K   Q   L   Q   A   R
1633  CAC CTG TTG CAA CTC ACA GTC TGG GGC ATC AAG CAG CTC CAG GCA AGA
      GTG GAC AAC GTT GAG TGT CAG ACC CCG TAG TTC GTC GAG GTC CGT TCT
```

FIG.2F

```
      V   L   A   L   E   R   Y   L   Q   D   Q   R   F   L   G   M
+1   GTC CTG GCT CTG GAA AGA TAC CTA CAG GAT CAA CCG TTC CTA GGG ATG
1681 CAG GAC CGA GAC CTT TCT ATG GAT GTC CTA GTT GCC AAG GAT CCC TAC

W   G   C   S   G   K   L   I   C   T   T   A   V   P   W   N
+1   TGG GGT TGC TCT GGA AAA CTC ATC TGC ACT ACT GCT GTG CCT TGG AAT
1729 ACC CCA ACG AGA CCT TTT GAG TAG TGA TGA CGA CAC GGA ACC TTA

A   S   W   S   N   K   N   L   S   Q   I   W   D   N   M   T
+1   GCT AGT TGG AGT AAT AAA AAT CTA AGT CAG ATT TGG GAT AAC ATG ACC
1777 CGA TCA ACC TCA TTA TTT TTA GAT TCA GTC TAA ACC CTA TTG TAC TGG

W   M   E   W   E   R   E   I   S   N   Y   T   E   I   I   Y
+1   TGG ATG GAG TGG GAG AGA GAA ATA AGC AAT TAC ACA GAG ATA ATT TAT
1825 ACC TAC CTC ACC CTC TCT CTT TAT TCG TTA ATG TGT CTC TAT TAA ATA

S   L   I   E   E   S   Q   N   Q   E   K   N   E   L   D
+1   AGC TTA ATT GAA GAA TCG CAG AAC CAA GAA AAG AAT GAA CTA GAC
1873 TCG AAT TAA CTT CTT AGC GTC TTG GTT CTT TTC TTA CTT GAT CTG

L   Q   L   D   K   W   A   S   L   W   N   W   F   D   I
+1   TTA CAA TTG GAT AAG TGG GCA AGT TTG TGG AAT TGG TTT GAC ATA
1921 AAT GTT AAC CTA TTC ACC CGT TCA AAC ACC TTA ACC AAA CTG TAT

T
+1   ACA
1969 TGT
```

Effector responses elicited by gene gun delivery of the plasmid, pCMV.gp140.BX08, into BALB/c mice Immunization: 0.7 ug pCMV.gp140.BX08 + 0.7 ug pCMV     0.7 ug pCMV.gp140.BX08 + 0.7 ug pCMV     1.4 ug pCMV In vitro re-stimulation: pulsed LPS blasts
  with autologous CLP-501 pulsed LPS blasts (■)
  with autologous LPS Blasts (▲)

with autologous CLP-504 pulsed LPS blasts (●)

with autologous CLP-501 pulsed LPS blasts (■)
  with autologous CLP-504 pulsed LPS blasts (●)

Target: CLP-501-pulsed P815     CLP-504-pulsed P815     CLP-501-pulsed P815 for CLP-501-pulsed blast re-stimulation
CLP-504-pulsed P815 for CLP-504-pulsed blast re-stimulation

FIG.4A    FIG.4B    FIG.4C

SEQUENCE LISTING

<160> NUMBER OF SEQ ID NOS: 14

<210> SEQ ID NO 1
<211> LENGTH: 1971
<212> TYPE: DNA
<213> ORGANISM: Human immunodeficiency virus type 1

<400> SEQUENCE: 1

| | | | | | | |
|---|---|---|---|---|---|---|
| atggatgcaa | tgaagagagg | gctctgctgt | gtgctgctgc | tgtgtggagc | a gtcttcgtt | 60 |
| tcggctagct | tgtgggtcac | agtctattat | ggggtacctg | tgtggaaaga | a gcaaccacc | 120 |
| actctatttt | gtgcatcaga | tgctaaagca | tatgatacag | aagtacataa | t gtttgggcc | 180 |
| acacatgcct | gtgtacccac | agaccccaac | ccacaagaag | tagtattggg | a aatgtgaca | 240 |
| gaaaatttta | acatggggaa | aaataacatg | gtagaacaga | tgcatgaaga | t ataattagt | 300 |
| ttatgggatc | aaagcctaaa | gccatgtgta | aaattaaccc | cactctgtgt | t actttaaat | 360 |
| tgcactaagt | tgaagaatag | tactgatacc | aataatacta | gatggggaac | a caagaaatg | 420 |
| aaaaactgct | ctttcaacat | cagcacaagt | gtaagaaata | agatgaagag | a gaatatgca | 480 |
| cttttttata | gtcttgatat | agtaccaata | gataatgata | tactagcta | t aggttaaga | 540 |
| agttgtaata | cctcaatcat | tacacaggcc | tgtccaaagg | tatcctttga | g ccaattccc | 600 |
| atacatttt | gtgccccggc | tggttttgcg | attctaaagt | gtaacaataa | a acgttcaat | 660 |
| ggaacaggac | catgtacaaa | tgtcagcaca | gtacaatgta | cacatggaat | t aggccagta | 720 |
| gtatcaactc | aactgctgtt | aaatggcagc | ctagcagaag | aagaggtagt | a attagatct | 780 |
| gaaaatttca | caaacaatgc | taaaaccata | atagtacagc | taaatgaatc | t gtagaaatt | 840 |
| aattgtacaa | gacccaacaa | caatacaaga | aaaagtatac | ataggacc | a gggagagca | 900 |
| ttttatacaa | caggagatat | aataggagat | ataagacaag | cacattgtaa | c attagtaga | 960 |
| acaaactgga | ctaacacttt | aaaaagggta | gctgaaaaat | taagagaaaa | a tttaataat | 1020 |
| acaacaatag | tctttaatca | atcctcagga | ggggacccag | aaattgtaat | g cacagtttt | 1080 |
| aattgtggag | ggaatttttt | ctactgtaat | acaacacaac | tgtttaatag | t acttggaat | 1140 |
| gaaactaaca | gtgaaggaaa | tatcaccagt | ggaactataa | cactcccatg | c agaataaaa | 1200 |
| caaattataa | acatgtggca | ggaagtagga | aaagcaatgt | atgcccctcc | c atcggagga | 1260 |
| caaattaaat | gttgtcaaa | catcacaggg | ctgttattaa | caagagatgg | t ggtagtgat | 1320 |
| aacagtagta | gtgggaaaga | gatcttcaga | cctggagggg | gagatatgag | g gacaattgg | 1380 |
| agaagtgaat | tatataaata | taaggtagta | aaaattgaac | cattaggaat | a gcacccacc | 1440 |
| aaggcaaaga | gaagagtggt | gcagagagaa | aaaagagcag | tgggaatagg | a gccatgttc | 1500 |
| cttgggttct | tgggagcagc | aggaagcact | atgggcgcag | cgtcactaac | g ctgacggta | 1560 |
| caggccagac | aattattgtc | tggtatagtg | cagcagcaaa | acaatttgct | g agggctatt | 1620 |
| gaggcgcaac | agcacctgtt | gcaactcaca | gtctggggca | tcaagcagct | c caggcaaga | 1680 |
| gtcctggctc | tggaaagata | cctacaggat | caacggttcc | tagggatgtg | g ggttgctct | 1740 |
| ggaaaactca | tctgcaccac | tgctgtgcct | tggaatgcta | gttggagtaa | t aaaaatcta | 1800 |
| agtcagattt | gggataacat | gacctggatg | gagtgggaga | gagaaataag | c aattacaca | 1860 |
| gagataatat | atagcttaat | tgaagaatcg | cagaaccaac | aagaaaagaa | t gaactagac | 1920 |
| ttattacaat | tggataagtg | ggcaagtttg | tggaattggt | ttgacataac | a | 1971 |

```
<210> SEQ ID NO 2
<211> LENGTH: 657
<212> TYPE: PRT
<213> ORGANISM: Human immunodeficiency virus type 1

<400> SEQUENCE: 2

Met Asp Ala Met Lys Arg Gly Leu Cys Cys Val Leu Leu Leu Cys Gly
  1               5                  10                  15

Ala Val Phe Val Ser Ala Ser Leu Trp Val Thr Val Tyr Tyr Gly Val
             20                  25                  30

Pro Val Trp Lys Glu Ala Thr Thr Thr Leu Phe Cys Ala Ser Asp Ala
         35                  40                  45

Lys Ala Tyr Asp Thr Glu Val His Asn Val Trp Ala Thr His Ala Cys
 50                  55                  60

Val Pro Thr Asp Pro Asn Pro Gln Glu Val Val Leu Gly Asn Val Thr
 65                  70                  75                  80

Glu Asn Phe Asn Met Gly Lys Asn Asn Met Val Gln Met His Glu
                 85                  90                  95

Asp Ile Ile Ser Leu Trp Asp Gln Ser Leu Lys Pro Cys Val Lys Leu
            100                 105                 110

Thr Pro Leu Cys Val Thr Leu Asn Cys Thr Lys Leu Lys Asn Ser Thr
        115                 120                 125

Asp Thr Asn Asn Thr Arg Trp Gly Thr Gln Glu Met Lys Asn Cys Ser
130                 135                 140

Phe Asn Ile Ser Thr Ser Val Arg Asn Lys Met Lys Arg Glu Tyr Ala
145                 150                 155                 160

Leu Phe Tyr Ser Leu Asp Ile Val Pro Ile Asp Asn Asp Asn Thr Ser
                165                 170                 175

Tyr Arg Leu Arg Ser Cys Asn Thr Ser Ile Ile Thr Gln Ala Cys Pro
            180                 185                 190

Lys Val Ser Phe Glu Pro Ile Pro Ile His Phe Cys Ala Pro Ala Gly
        195                 200                 205

Phe Ala Ile Leu Lys Cys Asn Asn Lys Thr Phe Asn Gly Thr Gly Pro
210                 215                 220

Cys Thr Asn Val Ser Thr Val Gln Cys Thr His Gly Ile Arg Pro Val
225                 230                 235                 240

Val Ser Thr Gln Leu Leu Leu Asn Gly Ser Leu Ala Glu Glu Val
                245                 250                 255

Val Ile Arg Ser Glu Asn Phe Thr Asn Asn Ala Lys Thr Ile Ile Val
            260                 265                 270

Gln Leu Asn Glu Ser Val Glu Ile Asn Cys Thr Arg Pro Asn Asn Asn
        275                 280                 285

Thr Arg Lys Ser Ile His Ile Gly Pro Gly Arg Ala Phe Tyr Thr Thr
290                 295                 300

Gly Asp Ile Ile Gly Asp Ile Arg Gln Ala His Cys Asn Ile Ser Arg
305                 310                 315                 320

Thr Asn Trp Thr Asn Thr Leu Arg Val Ala Glu Lys Leu Arg Glu
                325                 330                 335

Lys Phe Asn Asn Thr Thr Ile Val Phe Asn Gln Ser Ser Gly Gly Asp
            340                 345                 350

Pro Glu Ile Val Met His Ser Phe Asn Cys Gly Gly Glu Phe Phe Tyr
        355                 360                 365

Cys Asn Thr Thr Gln Leu Phe Asn Ser Thr Trp Asn Glu Thr Asn Ser
370                 375                 380
```

```
Glu Gly Asn Ile Thr Ser Gly Thr Ile Thr Leu Pro Cys Arg Ile Lys
385                 390                 395                 400

Gln Ile Ile Asn Met Trp Gln Glu Val Gly Lys Ala Met Tyr Ala Pro
                    405                 410                 415

Pro Ile Gly Gly Gln Ile Lys Cys Leu Ser Asn Ile Thr Gly Leu Leu
                420                 425                 430

Leu Thr Arg Asp Gly Gly Ser Asp Asn Ser Ser Ser Gly Lys Glu Ile
            435                 440                 445

Phe Arg Pro Gly Gly Gly Asp Met Arg Asp Asn Trp Arg Ser Glu Leu
        450                 455                 460

Tyr Lys Tyr Lys Val Val Lys Ile Glu Pro Leu Gly Ile Ala Pro Thr
465                 470                 475                 480

Lys Ala Lys Arg Arg Val Val Gln Arg Glu Lys Arg Ala Val Gly Ile
                485                 490                 495

Gly Ala Met Phe Leu Gly Phe Leu Gly Ala Ala Gly Ser Thr Met Gly
                500                 505                 510

Ala Ala Ser Leu Thr Leu Thr Val Gln Ala Arg Gln Leu Leu Ser Gly
            515                 520                 525

Ile Val Gln Gln Gln Asn Asn Leu Leu Arg Ala Ile Glu Ala Gln Gln
530                 535                 540

His Leu Leu Gln Leu Thr Val Trp Gly Ile Lys Gln Leu Gln Ala Arg
545                 550                 555                 560

Val Leu Ala Leu Glu Arg Tyr Leu Gln Asp Gln Arg Phe Leu Gly Met
                565                 570                 575

Trp Gly Cys Ser Gly Lys Leu Ile Cys Thr Thr Ala Val Pro Trp Asn
                580                 585                 590

Ala Ser Trp Ser Asn Lys Asn Leu Ser Gln Ile Trp Asp Asn Met Thr
            595                 600                 605

Trp Met Glu Trp Glu Arg Glu Ile Ser Asn Tyr Thr Glu Ile Ile Tyr
        610                 615                 620

Ser Leu Ile Glu Glu Ser Gln Asn Gln Gln Glu Lys Asn Glu Leu Asp
625                 630                 635                 640

Leu Leu Gln Leu Asp Lys Trp Ala Ser Leu Trp Asn Trp Phe Asp Ile
                645                 650                 655

Thr

<210> SEQ ID NO 3
<211> LENGTH: 10
<212> TYPE: PRT
<213> ORGANISM: Human immunodeficiency virus type 1

<400> SEQUENCE: 3

Ile Gly Pro Gly Arg Ala Phe Tyr Thr Thr
 1               5                  10

<210> SEQ ID NO 4
<211> LENGTH: 9
<212> TYPE: PRT
<213> ORGANISM: Human immunodeficiency virus type 1

<400> SEQUENCE: 4

Ala Tyr Asp Thr Glu Val His Asn Val
 1               5

<210> SEQ ID NO 5
<211> LENGTH: 9
<212> TYPE: PRT
```

-continued

```
<213> ORGANISM: Human immunodeficiency virus type 1

<400> SEQUENCE: 5

Phe Tyr Ser Leu Lys Ile Val Pro Ile
1 5

<210> SEQ ID NO 6
<211> LENGTH: 9
<212> TYPE: PRT
<213> ORGANISM: Human immunodeficiency virus type 1

<400> SEQUENCE: 6

Leu Tyr Lys Tyr Lys Val Val Lys Ile
1 5

<210> SEQ ID NO 7
<211> LENGTH: 10
<212> TYPE: PRT
<213> ORGANISM: Human immunodeficiency virus type 1

<400> SEQUENCE: 7

Lys Tyr Lys Val Val Lys Ile Glu Pro Leu
1 5 10

<210> SEQ ID NO 8
<211> LENGTH: 9
<212> TYPE: PRT
<213> ORGANISM: Human immunodeficiency virus type 1

<400> SEQUENCE: 8

Arg Tyr Leu Gln Asp Gln Arg Phe Leu
1 5

<210> SEQ ID NO 9
<211> LENGTH: 9
<212> TYPE: PRT
<213> ORGANISM: Human immunodeficiency virus type 1

<400> SEQUENCE: 9

Asn Tyr Thr Glu Ile Ile Tyr Ser Leu
1 5

<210> SEQ ID NO 10
<211> LENGTH: 9
<212> TYPE: PRT
<213> ORGANISM: Human immunodeficiency virus type 1

<400> SEQUENCE: 10

Lys Leu Thr Pro Leu Cys Val Thr Leu
1 5

<210> SEQ ID NO 11
<211> LENGTH: 9
<212> TYPE: PRT
<213> ORGANISM: Human immunodeficiency virus type 1

<400> SEQUENCE: 11

Thr Leu Phe Arg Val Ala Ile Lys Leu
1 5

<210> SEQ ID NO 12
<211> LENGTH: 9
<212> TYPE: PRT
<213> ORGANISM: Human immunodeficiency virus type 1
```

-continued

```
<400> SEQUENCE: 12

Thr Leu Thr Val Gln Ala Arg Gln Leu
  1               5

<210> SEQ ID NO 13
<211> LENGTH: 9
<212> TYPE: PRT
<213> ORGANISM: Human immunodeficiency virus type 1

<400> SEQUENCE: 13

Thr Leu Thr Val Gln Ala Arg Ala Leu
  1               5

<210> SEQ ID NO 14
<211> LENGTH: 9
<212> TYPE: PRT
<213> ORGANISM: Human immunodeficiency virus type 1

<400> SEQUENCE: 14

Gln Leu Gln Ala Arg Val Leu Ala Leu
  1               5
```

EXPRESSING GP140 FRAGMENT OF PRIMARY HIV-1 ISOLATE

FIELD OF INVENTION

The present invention relates to the field of immunology, specifically HIV Vaccine Technology, and, in particular, is concerned with expressing the extracellular fragment of the envelope gene, gp140, of a primary human immunodeficiency virus type 1 (HIV-1) isolate.

BACKGROUND OF THE INVENTION

Acquired immunodeficiency syndrome (AIDS) is a disease which is the ultimate result of infection with human immunodeficiency virus (HIV). Currently, there is no effective vaccine which can protect the human population from HIV infection and hence the development of an efficacious HIV-vaccine and protocol for administering the same is urgently required. Previously, HIV-1 particles exhaustively inactivated by chemical treatments, a vaccinia vector encoding the whole envelope gene (gp140) of HIV-1, and purified recombinant gp120 have been evaluated as candidate HIV vaccines. Although inactivated HIV-1 virus preparations elicited a T-cell-mediated Delayed-Type Hypersensitivity (DTH) reaction in humans, and vaccinia/gp160 and gp120 recombinant vaccine candidates induced virus neutralizing antibodies, non of these immunogens have been shown to be efficacious human HIV vaccines (ref. 1, throughout this specification, various references are referred to in parenthesis to more fully describe the state of the art to which this invention pertains. Full bibliographic information for each citation is found at the end of the specification, immediately following the claims. The disclosures of these references are hereby incorporated by reference into the present disclosure). The inventors' interest in HIV vaccinology is to develop immunogenic and cost-effective HIV-1 DNA vaccines and consider that their use alone or in conjunction with other forms of HIV-1 vaccine candidates will lead to the elicitation of more effective immune responses against HIV-1.

There has previously been described in granted European Patent No. 470,980 and U.S. Pat. No. 5,639,854, assigned to the assignee hereof, the disclosures of which are incorporated herein by reference, inter alia, the identification and characterization of a T-cell epitope of the core protein, p24E, of HIV-1. There has further been described in granted U.S. Pat. Nos. 5,759,769 and 5,795,955, assigned to the assignee hereof, and disclosures of which are incorporated by reference, the use of the T-cell epitope in the construction of immunogenic synthetic HIV-1 chimeric peptides comprising p24E linked to amino acid sequences of different B-cell epitopes of an envelope or core protein of HIV-1.

SUMMARY OF THE INVENTION

The present effort has turned to design and construct HIV DNA-based immunogens capable of eliciting cell-mediated immunity (CMI). In this context, the inventors have focused interest on the extracellular envelope fragment, gp140, expressed in a primary HIV-1 isolate, HIV-1 (BX08), for the reason that this protein is rich in motifs restricted to both the murine and human Major Histocompatibility Complex (MHC) class 1 alleles. Upon immunization with an appropriately constructed immunogen expressing the gp140 protein leads to the generation of peptides with class 1 binding capability to allow the induction of HIV-1-specific CTLs capable of killing virus infected cells to limit infection.

The invention described by the inventors is that they have found a plasmid designated, pCMV.gp140.BX08, expressing the gp140 gene under the control of a CMV promotor was immunogenic in BALB/c mice in the elicitation of CTL response directed against multiple epitopes of the gp140 protein that are restricted to different $H-2^d$ class 1 gene products.

Accordingly, in one aspect of the present invention, there is provided a vector, comprising a gene encoding the extracellular fragments of gp140 of a primary HIV-1 isolate, preferably BX08, under the control of a promotor for expression of the gene product in a host organism, thereby eliciting a cytotoxic T-cell response.

Figure 1:
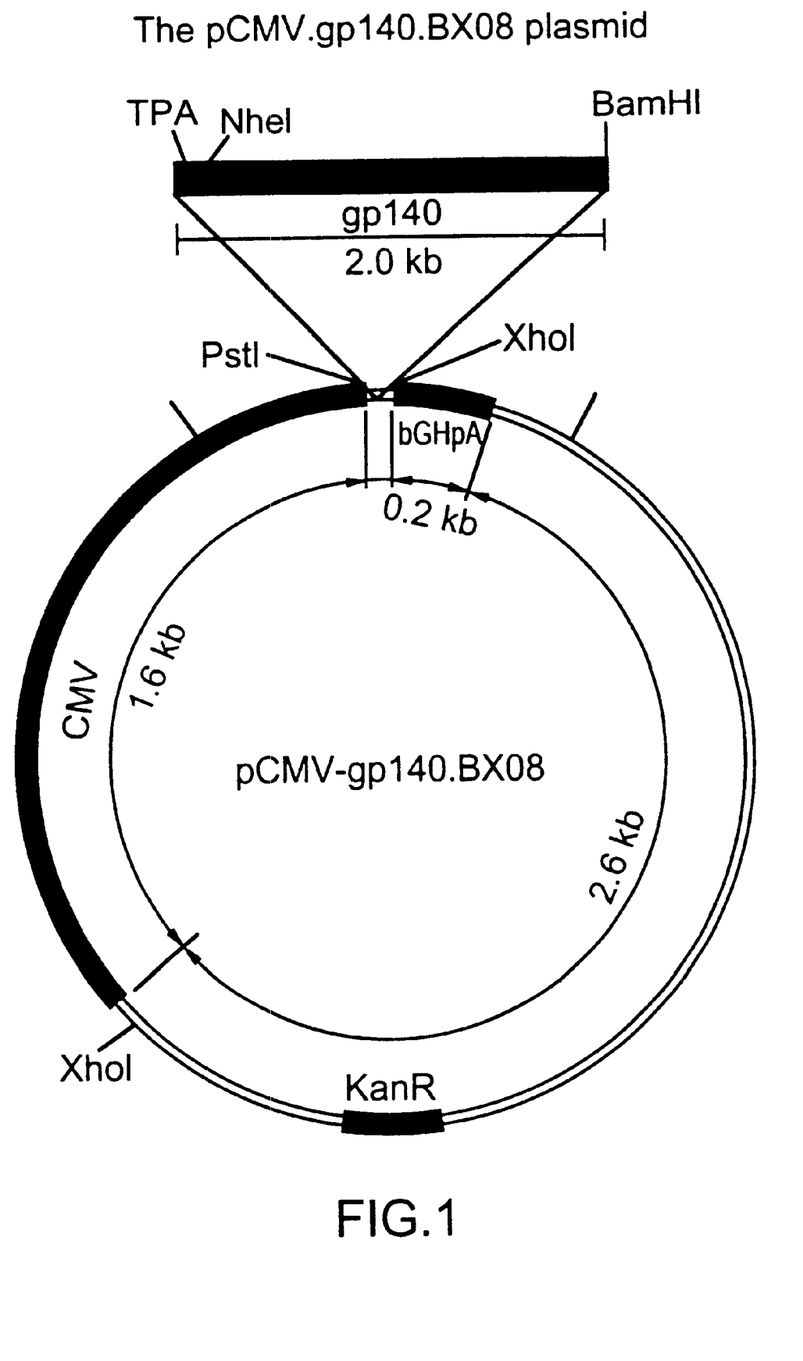
FIG. 1 shows details of the elements of plasmid pCMV.gp140.BX08.
Figure 2A:
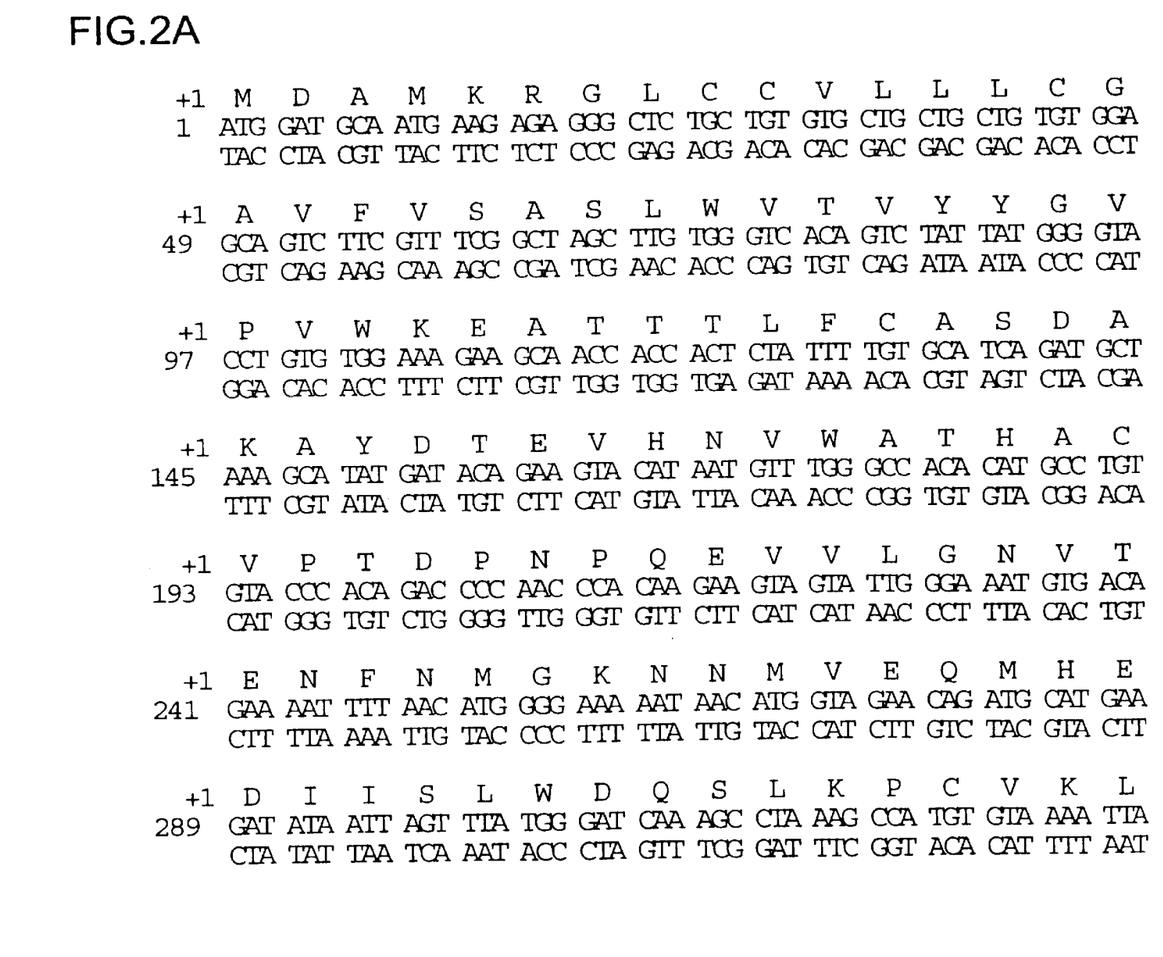
FIGS. 2A to 2F show the nucleotide (SEQ ID No: 1) and deduced amino acid sequence (SEQ ID No: 2) of the gp140 open reading frame of the plasmid pCMV.gp140.BX08.
Figure 2B:
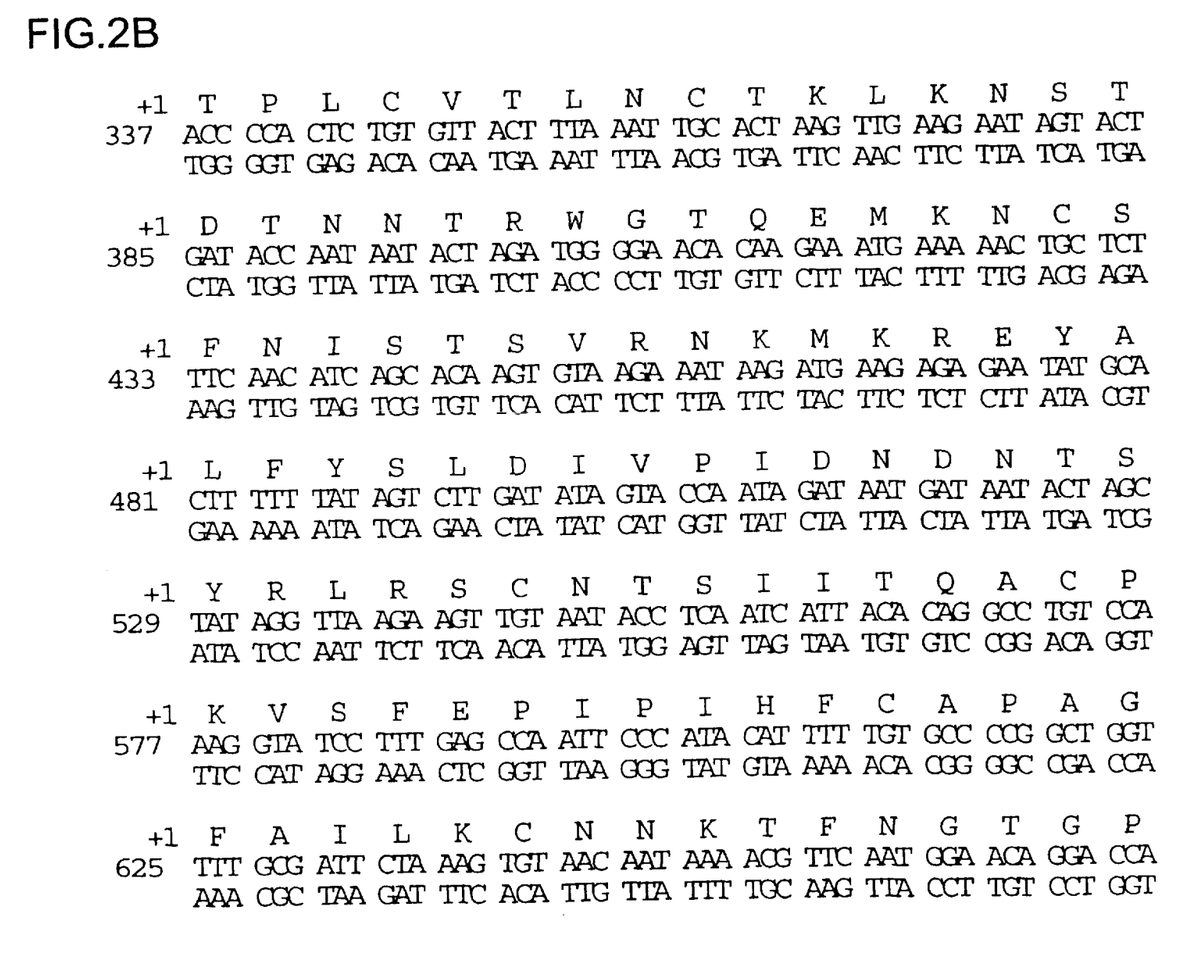
Figure 2C:
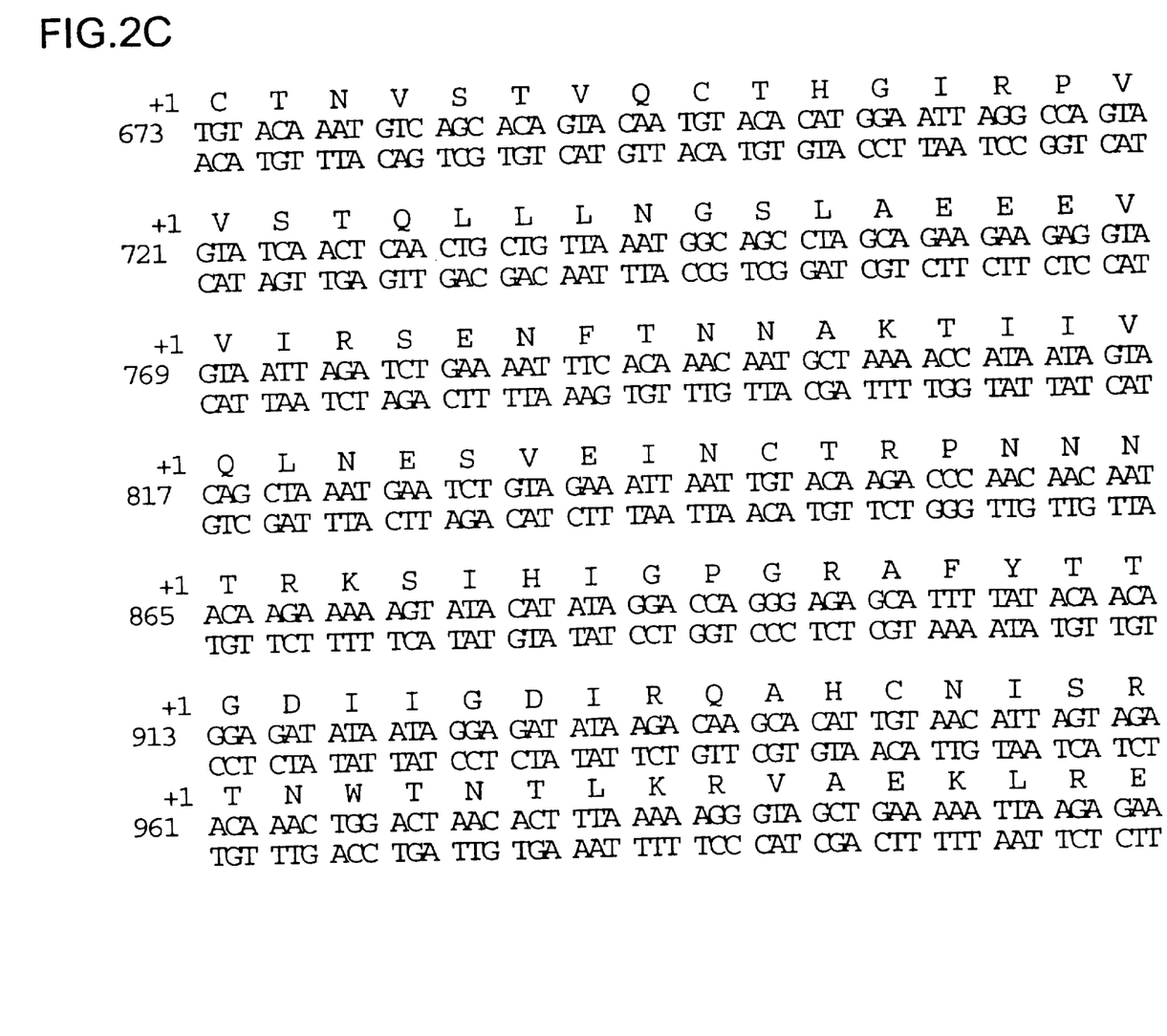
Figure 2D:
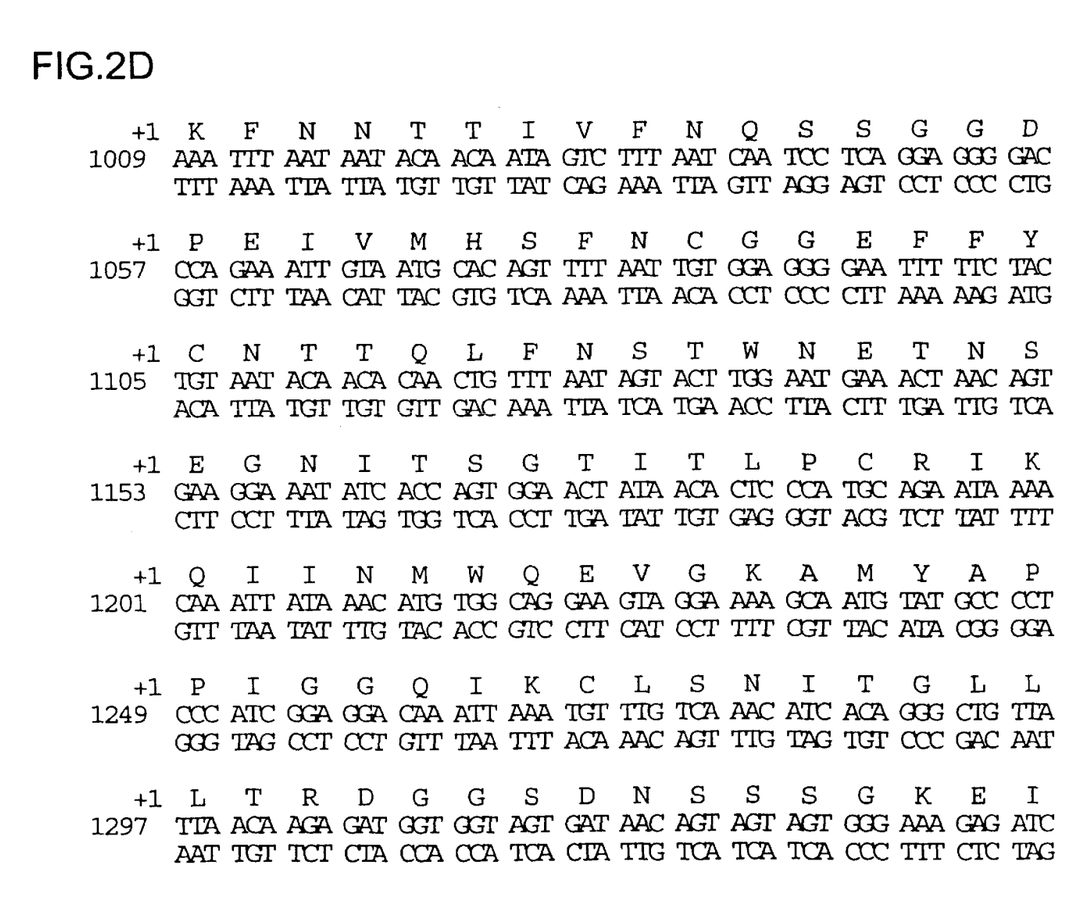
Figure 2E:
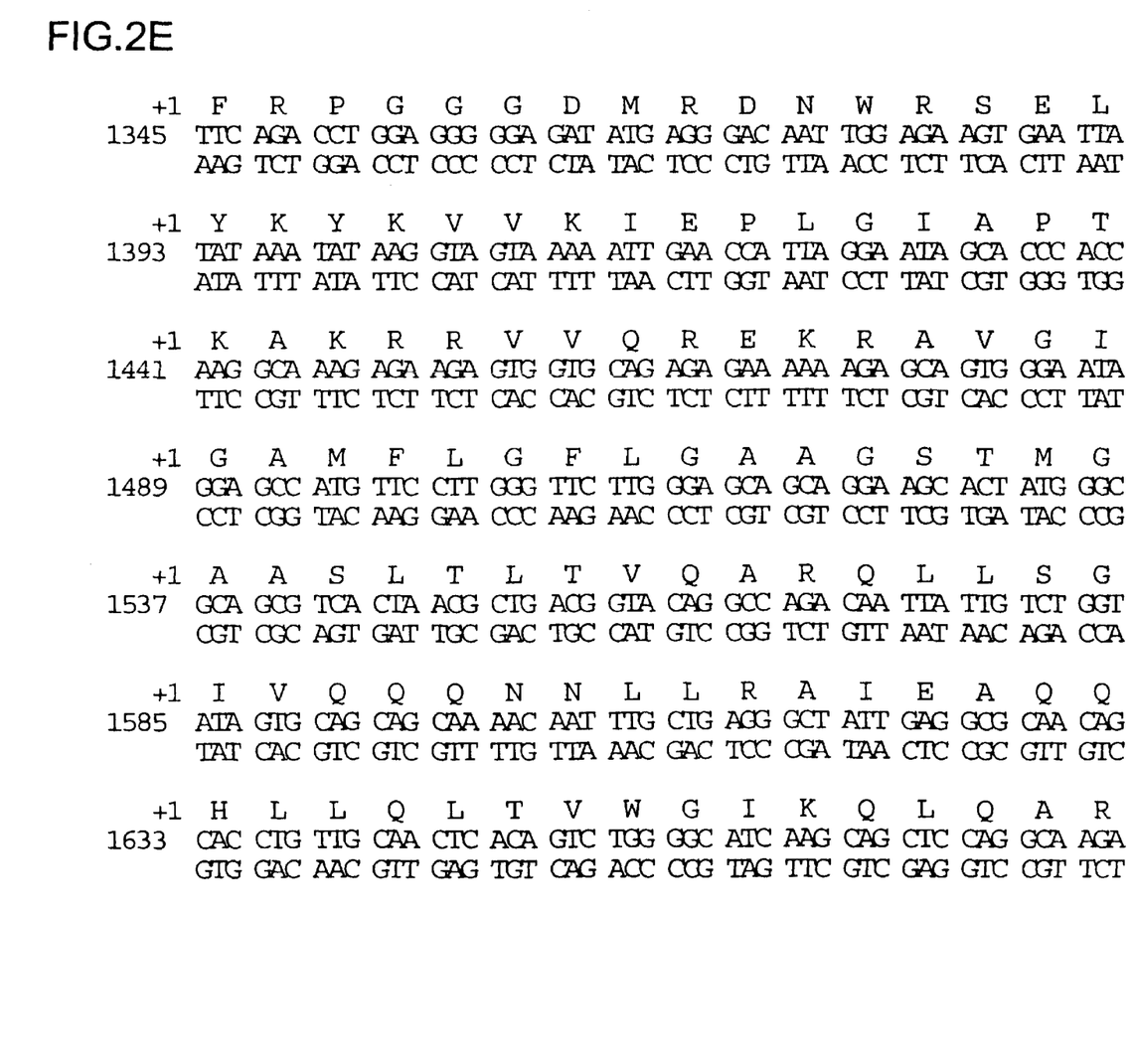
Figure 2F:
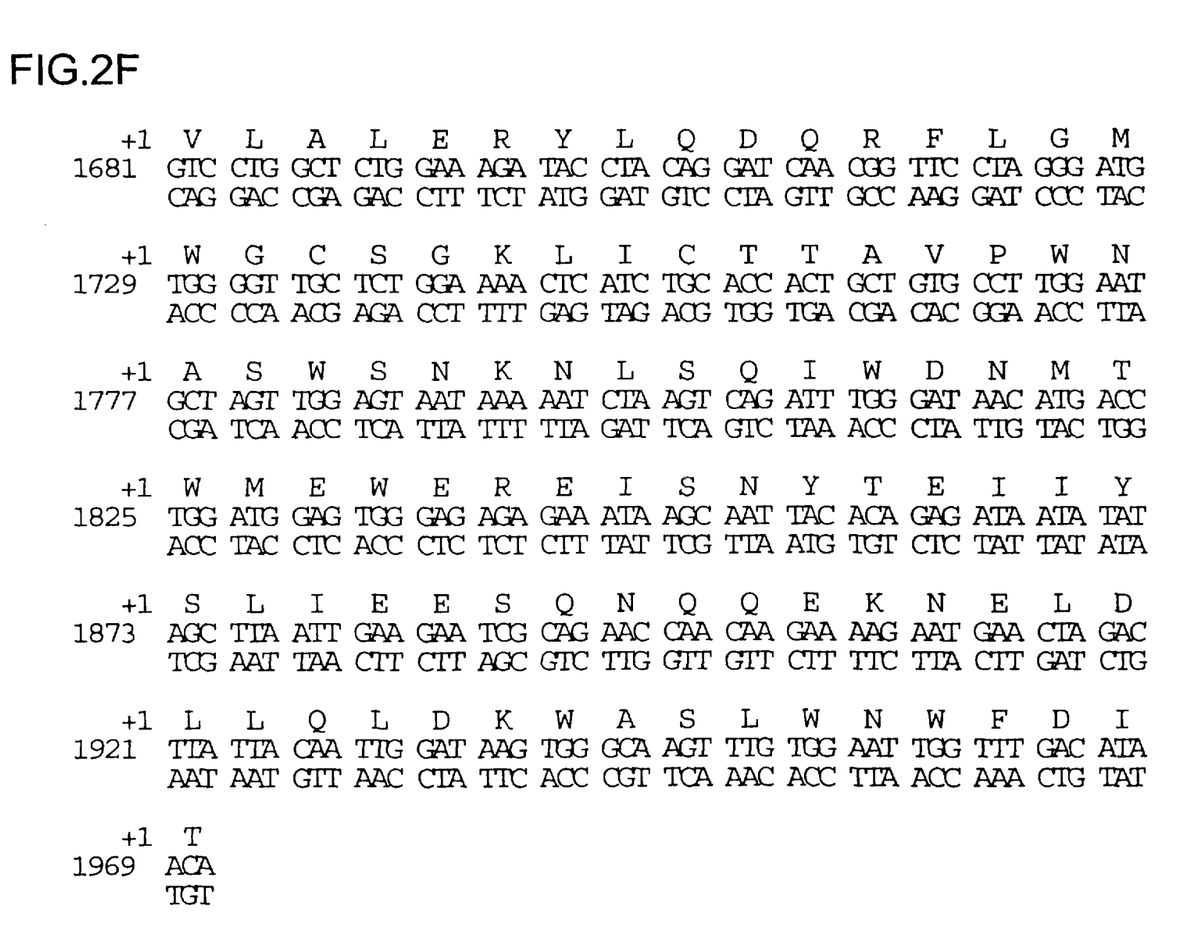

The promotor thereby is the cytomegalovirus promotor. The vector is preferably one having the identifying characteristics of plasmid pCMV.gp140.BX08, as shown in FIG. 1.

The invention further includes an immunogenic composition containing the vector as well as a method of generating a cytotoxic T-cell response in a host by administering to the host the immunogenic composition provided herein. Such immunogenic composition may be formulated for intramuscular immunization with a suitable carrier or may be formulated for gene gun delivery with gold particles.

DETAILED DESCRIPTION OF THE INVENTION

A DNA immunogen is constructed using recombinant DNA technology to molecularly clone a gene of interest into a plasmid expression vector. A unique feature involving vaccination with a DNA-based immunogen is that, once delivered into a cell, the intracellular production of the immunogen favours the induction of MHC class 1-restricted cytotoxic T-cells as compared to other forms of vaccination involving the use of killed whole cell and formulated sub-unit immunogens, which tend to favour the elicitation of MHC class 2-restricted immuno-regulatory responses in the majority of cases studied (ref. 2). In this context, it is, therefore, favourable to use DNA technology to construct naked DNA immunogens for vaccination purposes in order to optimize the induction of cellular effector response against intracellular organisms, such as viruses as well as certain tumours. The other advantages DNA vaccines offer include: (i) the ease to produce; and (ii) their stability over a wide temperature range.

A common model which has been used recently to predict murine and human CTL antigenic determinants has involved the identification of binding motifs for the respective MHC class 1 molecules from the primary sequences of the native protein molecules (see refs. 3 to 5). Thus, it has been proposed that motifs which are most favoured to bind and lodge into the peptide-binding groove of the H-2D$^d$ gene product is usually 8 to 10 amino acids long. In the majority of cases, these peptides are found to contain anchor residues, such as glycine and proline (GP), at positions 2 and 3 near the amino- (N-) terminus, and either a leucine or phenylalanine at the carboxy- (C-) terminus, which serve to interact with the respective 'pockets' of the peptide-binding groove of a membrane-bound H-2D$^d$ molecule. The motifs restricted to the other class 1 allele, K$^d$, of the H-2$^d$ haplotype were reported to contain a tyrosine at position 2, and could be an isoleucine, valine or leucine at the C-terminus. Studies of the peptides isolated from the human MHC class 1 molecules, HLA-A0201, had similarly revealed that the anchor residues were leucine or methionine at position 2 and valine or leucine at the C-terminus in the majority of cases.

The suitability of the HIV-1(BX08) gp140 gene product as a CTL-inducing immunogen was assessed by prediction algorithms to determine the number of both the murine and human MHC class 1-restricted binding motifs it contained. The amino acid sequences of the binding motifs and the designation of the peptides representing them are shown in Table 1 below. The presence of binding motifs towards the different H-2$^d$ restricted class 1 alleles, i.e. D$^d$ and K$^d$, allows the immunogenicity of a plasmid, pCMV.gp140.BX08, expressing gp140 of HIV-1 of the primary isolate, BX08, and constructed as described in the Example below, to be studied in the inbred mouse strain BALB/c of the H-2$^d$ hapotype. The elements and restriction sites of plasmid pCMV.gp140.BX08 are shown in FIG. 1. The nucleotide (SEQ ID No: 1) and the deduced amino acid sequences (SEQ ID No: 2) of the gp140 open reading frame of the plasmid pCMV.gp140.BX08 is shown in FIGS. 2A to 2F, which appear to be unique sequences.

The location of several binding motifs against the human MHC class 1 allele, HLA-A0201, as seen in Table 1, implied that, under an appropriate immunization regimen, the plasmid has the potential to elicit CTL response directed to these epitopes in the context of this class 1 molecule in human subjects.

Figure 3A:
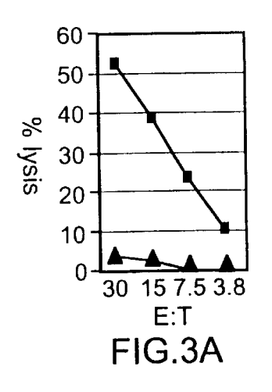
FIGS. 3A, 3B and 3C show the effector responses elicited by intramuscular injection of the plasmid, pCMV.gp140.BX08, in BALB/c mice.
Figure 3B:
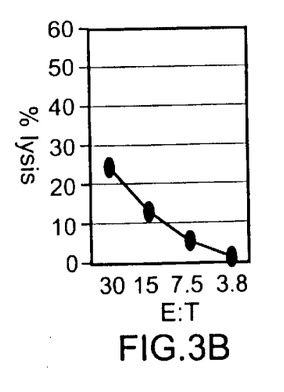
Figure 3C:
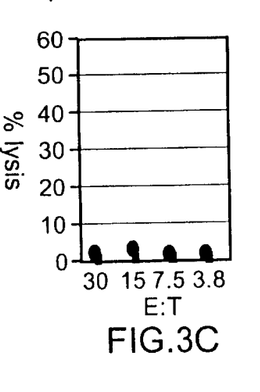

The immunogenicity of the plasmid pCMV.gp140.BX08 was studied in BALB/c mice. The results of the study involving three injections of the plasmid at 100.0 µg per dose using the intramuscular route are shown in FIG. 3. Upon in vitro re-stimulation of the spleenocytes of the plasmid-immunized animals with irradiated autologous LPS blasts pulsed individually with the D$^d$- and K$^d$-restricted motif containing peptides, namely, CLP-501 and CLP-504 (SEQ ID Nos.: 3, 5), respectively, it was found that CTLs were generated that killed P815 targets presented with the respective peptides (FIGS. 3A and 3B). The amino acid sequences of the peptides are shown in Table 1. A comparison of the magnitude of the responses at the same effector to target (E:T) ratio revealed that the D$^d$-restricted response to the CLP-501 peptide is immuno-dominant and that the K$^d$-restricted response to the CLP-504 peptide is subdominant. The in vitro re-stimulating leading to the expansion of the effectors was specific because the addition of the same number of irradiated LPS blasts alone (not treated with peptide) did not lead to any generation of effectors in the bulk culture able to kill either of the specific targets tested. The findings that the control group of mice injected with the pCMV vector without the gp140 insert alone failed to generate any of the two sub-populations of CTLs (FIG. 3C) confirmed that the plasmid, pCMV.gp140.BX08, was indeed immunogenic.

Figure 4A:
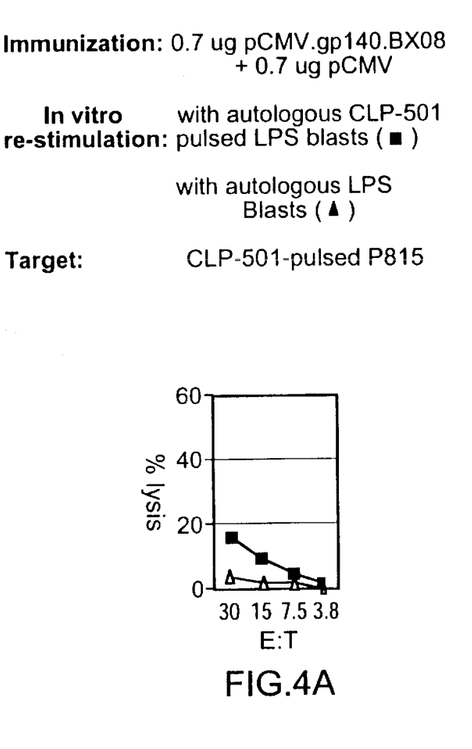
FIGS. 4A, 4B and 4C show the effector responses elicited by gene gun delivery of the plasmid, pCMV.gp140.BX08, in BALB/c mice.
Figure 4B:
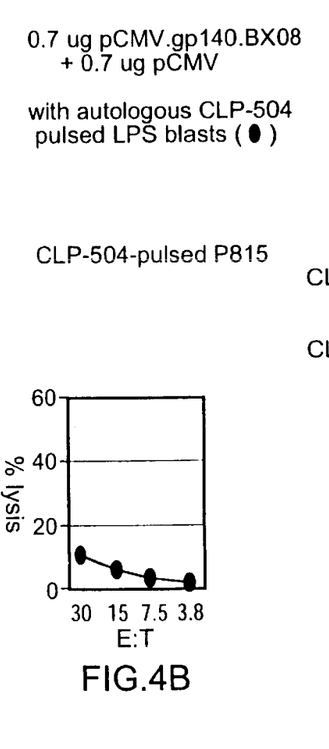
Figure 4C:
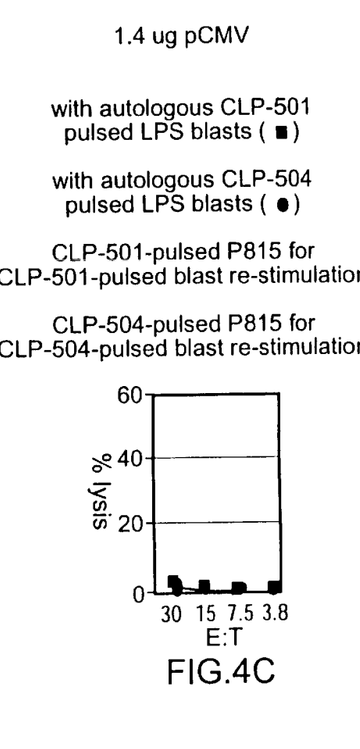

The pCMV.gp140.BX08 plasmid, when delivered with the gene gun, was similarly found to be immunogenic. The results shown in FIG. 4 show that following two injections at a dose of 0.7 µg of the plasmid, and using the same in vitro re-stimulation condition described above that CTLs recognizing the CLP-501 and CLP-504 peptides were detected (FIGS. 4A and 4B), while no effector response was elicited by the group of animals given the vector, pCMV, alone (FIG. 4C).

It is clearly apparent to one skilled in the art, that the various embodiments of the present invention have many applications in the fields of vaccination, diagnosis and treatment of HIV infections. A further non-limiting discussion of such uses is further presented below.

Immunogenic compositions, including vaccines, containing the DNA vector may be prepared as injectables, in physiologically-acceptable liquid solutions or emulsions for polynucleotide administration. The DNA vector may be associated with liposomes, such as lecithin liposomes or other liposomes known in the art, as a nucleic acid liposome (for example, as described in WO 93/24640) or the DNA vector may be associated with an adjuvant, as described in more detail below.

Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides.

Agents which assist in the cellular uptake of nucleic acid, such as calcium ions, viral proteins and other transfection facilitating agents, may advantageously be used with the vector.

Polynucleotide immunogenic preparation may also be formulated as microcapsules, including biodegradable time-release particles. Thus, U.S. Pat. No. 5,151,264 describes a particular carrier of a phospholipid/glycolipid/polysaccharide nature that has been termed Bio Vecteurs Supra Moléculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactidecoglycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain and absorption enhancer.

In particular embodiments of the present invention, the vector may be delivered in conjunction with a targeting molecule to target the vector to selected cells including cells of the immune system.

The vectors may be delivered to the host by a variety of procedures, for example, Tang et al (ref. 6) discloses that introduction of gold microprojectiles coated with DNA encoding bovine growth hormone (BGH) into the skin of mice resulted in production of anti-BGH antibodies in the mice, while Furth et al. (ref. 7) showed that a jet injector could be used to transfect skin, muscle, fat and mammary tissues of living animals.

Biological Deposits

Certain vectors that contain nucleic acid coding for a high molecular weight protein of a non-typeable strain of Haemophilus that are described and referred to herein have been deposited with the America Type Culture Collection (ATCC) located at 10801 University Boulevard, Manassas, Va. 20110-2209, USA, pursuant the Budapest Treaty and prior to the filing of this application. Samples of the deposited vectors will become available to the public and all restrictions imposed or access to the deposits will be received upon grant of a patent based on this United States patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

| Deposit Summary | | |
|---|---|---|
| Plasmid | ATCC | Deposited Date |
| pCMV.gp140.BX08 | 203839 | March 9, 1999 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of plasmid construction, peptide synthesis, cell culture, CTL assay and other testing procedures that are not explicitly described in this disclosure are amply reported in the scientific literature and are will within the scope of those skilled in the art.

Example 1

This Example illustrates the construction of the plasmid, pCMV.gp140.BX08.

The plasmid, pCMV.gp140.BX08, contains sequence segments from various sources, and the elements of construction are depicted in FIG. 1. The nucleotide (SEQ ID No: 1) and derived amino acid sequences (SEQ ID No: 2) of the gp140 open reading frame of the plasmid are shown in FIGS. 2A to 2F.

The prokaryotic vector pBluescript SK (Stratagene) is the backbone of the plasmid pCMV.gp140.BX08 and was modified by the replacement of the $Amp^R$ with $Kan^R$ gene and the deletion of the f1 and the LacZ region. To achieve the desired modifications, the sequence between Ahdl (nucleotide 2,041) and SacI (nucleotide 759) of pBluescript SK, which contains the $Amp^R$, f1 origin and the LacZ, was deleted. A 1.2 kb PstI fragment from the plasmid pUC-4K (Pharmacia) containing the $Kan^R$ gene, was blunt end ligated to the Ahdl site of pBluescript SK in a counter-clockwise orientation relative to it's transcription. A 1.6 kb SspI/PstI DNA fragment containing the human cytomegalovirus immediate-early gene promotor, enhancer and intron A sequences (CMV) was ligated to the other end of the $Kan^R$ gene so that the transcription from the CMV promotor proceeds in the clockwise orientation. A synthetic oligonucleotide segment containing translation initiation sequence and sequences encoding the human tissue plasminogen activator signal peptide (TPA) was used to link the CMV promotor and the sequences encoding the gp140 of the primary isolate HIV-$1_{BX08}$. The gp140 sequence encodes a portion of the envelope protein between amino acid 33 and 666 which ends before the transmembrane domain of gp41 (see FIG. 2). A translation termination codon was placed at the end of the gp140 coding sequence. Next to the gp140 coding region is a 0.2 kb fragment containing the bovine growth hormone (BGH) polyadenylation signal sequence that is PCR amplified from pRC/CMV (Invitrogen). A remnant 80 bp DNA segment from the SV40 polyadenylation signal remained between the BGH poly A sequence and the SacI site of pBluescript SK due to DNA manipulation and it serves no purpose in this plasmid.

The pCMV.gp140.BX08 construct was introduced into HB101 competent cells according to manufacturer's recommendations (GibcoBRL). Correct molecular clones were identified by restriction and sequencing analysis and their expression of gp140 was examined in transient transfections followed by Western blot analysis.

All DNAs used for immunizations were prepared using EndoFree Plasmid Kit (Qiagen). For intramuscular immunizations in mice, 100 µg of pCMV.gp140.BX08, in 100 µl PBS was injected into the tibialis anterior muscles at 4 weeks intervals. Gene gun immunizations were accomplished with the Helios Gene Gun System (Biorad). Cartridges were prepared according to manufacturer's recommendations. Specifically, each cartridge was made to contain 0.7 μg of the DNA and 0.5 mg gold. Immunizations were carried out by applying two cartridges to each animal onto the shaved abdominal area at 4 week intervals.

Example 2

This Example illustrates the synthesis of peptides.

Solid phase peptide synthesis of peptide CLP-501 and CLP-504 were conducted on an ABI 430A automated peptide synthesizer according to the manufacturer's standard protocols. The peptides were cleaved from solid support by treatment with liquid hydrogen fluoride in the presence of thiocresole, anisole, and methyl sulfide. The crude products were extracted with trifluoroacetic acid (TFA) and precipitated with diethyl ether.

The amino acid sequences of these peptides are shown in Table 1.

Example 3

This Example illustrates in vitro cell culture protocols to re-stimulate and expand CTLs and assay for their effector functions.

Spleens of BALB/c mice injected with the plasmid, pCMV.gp140.BX08, prepared and formulated as described in Example 1, using the intramuscular route or gene gun delivery method, were removed 10 to 11 days post final booster injection. Spleenocytes at $3.0 \times 10^7$ were co-cultured with $1.3 \times 10^7$ autogolous LPS blasts which had been pulsed with the test peptide for 5 hr at 37° C. and irradiated at 3000 rads in 10.0 ml of complete medium (RPMI 1640 supplemented with 10.0% 56° C. heat-inactivated bovine serum, 120.0 units per ml of penicillin G sodium, 120.0 μg per ml of streptomycin sulphate and 0.35 mg per ml of L-glutamine) in a 25 cm² tissue culture flask. The cultures were kept at 37° C. in a humidified $CO_2$ incubator for days, and the responders were then tested against peptide-pulsed P815 target cells in a standard in vitro 4 hr CTL assay as follows:

The responders were harvested from the 7-day cultures and washed once with RPMI 1640 medium without added bovine serum. The positive target was created by incubating 3 to $5 \times 10^6$ P815 cells with 100.0 μg of the specified peptide overnight in a 26° C. water bath. The target cells were then labeled with $^{51}Cr$ at 250.0 uCi per $1 \times 10^6$ cells in the presence of 25.0 μg of the same test peptides for 60 to 75 minutes at 26° C. After washing twice with complete medium to remove excess $^{51}Cr$, the targets were incubated at $2.5 \times 10^3$ with different numbers of the responders per well in a V-bottomed 96 will tissue culture plates for 4 hr in a 37° C. $CO_2$ incubator. Half amount of the supernatant from each micro-assay culture was then removed and counted for radioactivity. Results were expressed as % which was calculated using the equation:

% lysis=(spontaneous lysis in cpm of experimental sample–spontaneous lysis in cpm of labeled target cells alone) devided by (totally lysis in com of target cells alone–spontaneous lysis in cpm of target cells alone)×100.

The results obtained employing intramuscular injection are shown in FIGS. 3A, 3B and 3C while those obtained employing the gene gun delivery are shown in FIGS. 4A, 4B and 4C and are disable alone.

SUMMARY OF DISCLOSURE

In summary of this disclosure, the present invention provides a novel plasmid expressing, in vitro and in vivo, the gp140 protein of the primary HIV-1 isolate BX08 and the generation of MHC class 1-restricted cytotoxic T-cells in animals. Modifications are possible within the scope of this invention.

TABLE 1

MHC class 1-restricted motifs of the extracellular envelope fragment, gp140, of HIV-1(BX08)

H-2$^d$-restricted *

| Peptide *** D$^d$- | Peptide *** K$^d$- | | HLA-A0201-restricted ** | |
|---|---|---|---|---|
| CLP-501 IGPGRAFYTT (274–283) (SEQ ID No:3) | CLP-503 AYDTEVHNV (29–37) (SEQ ID No:4) | | KLTPLCVTL (91–98) (SEQ ID No:10) | |
| | CLP-504 FYSLKIVPI (141–149) (SEQ ID No:5) | | TLFRVAIKL (305–313) (SEQ ID No:11) | |
| | CLP-505 LYKYKVVKI (443–451) (SEQ ID No:6) | | TLTVQARQL (403–411) (SEQ ID No:12) | |
| | CLP-506 KYKVVKIEPL (445–454) (SEQ ID No:7) | | TLTVQARAL (496–504) (SEQ ID No:13) | |
| | CLP-507 RYLQDQRFL (545–553) (SEQ ID No:8) | | QLQARVLAL (535–543) (SEQ ID No:14) | |
| | CLP-508 NYTEIIYSL (597–605) (SEQ ID No:9) | | | |

* or ** Anchors residues were typed in bolded letters
*** Peptides chosen for the study reported herein are bolded.

REFERENCES

1. B. J. Spalding. Biotechnology, vol. 10, pp 24–28, 1992
2. H. L. Robinson and C. A. T. Torres. Seminars in Immunology, vol. 9, pp 271–283, 1997.
3. Ian A. Wilson and Daved H. Fremont. Seminars in Immunology, vol. 5, pp 75–80, 1993.
4. Kristen Falk and Olaf Rotzschke. Seminars in Immunology. Vol. 5, pp 81–94, 1993.
5. Victor H. Englefard. Current Opinion in Immunology, Vol. 6, pp 13–23, 1994.
6. Tang et al, Nature, 1992, 356:152–154.
7. Furth et al, Analytical Biochemistry, 1992, 205:365–368.

What is claimed is:

1. A method of generating a cytotoxic T-cell response in a host, which comprises administering to the host an immunogenic composition comprising a plasmid vector comprising a gene encoding the extracellular fragment of gp140 of the primary HIV-1 isolate BX08 under the control of a promoter which expresses the gene product in the host.

2. The method of claim 1, wherein the promoter is the cytomegalovirus promotor.

3. The method of claim 1 wherein the plasmid vector is pCMV.gp140.BX08 (ATCC No. 203839).

4. A vector which is pCMV.gp140.BX08 (ATCC No. 203839), as shown in FIG. 1.

5. An immunogenic composition comprising a vector which is pCMV.gp140.BX08 (ATCC No. 203839).

6. The immunogenic composition of claim 5 formulated for intramuscular immunization with a pharmaceutically-acceptable liquid carrier.

7. The immunogenic composition of claim 5 formulated for gene gun delivery with gold particles.

* * * * *